United States Patent [19]

Brown

[11] 4,078,266
[45] Mar. 14, 1978

[54] CAST SOCK

[76] Inventor: Nancy Burroughs Brown, 9701 Fields Rd., Apt. 1005, Gaithersburg, Md. 20760

[21] Appl. No.: 705,260

[22] Filed: Jul. 14, 1976

[51] Int. Cl.$^2$ ............................................. A41B 11/00
[52] U.S. Cl. ...................................... 2/240; 128/83.5
[58] Field of Search ................ 2/240, 239; 66/178 R, 66/185; 128/83.5, 83

[56] References Cited

U.S. PATENT DOCUMENTS

| | | | |
|---|---|---|---|
| 2,514,108 | 7/1950 | Vogt | 2/240 X |
| 2,703,405 | 3/1955 | Smallberg | 2/239 |
| 2,730,720 | 1/1956 | Saunders | 2/240 X |
| 2,800,662 | 7/1957 | Rosecrans | 2/240 |

*Primary Examiner*—H. Hampton Hunter
*Attorney, Agent, or Firm*—Stevens, Davis, Miller & Mosher

[57] ABSTRACT

A toe covering for use with a surgical cast comprising an open ended semi-sock body of knitted textile material, adapted to receive the forward portion of a human foot extending beyond the cast and portions of flexible gripping material spaced around the interior of the body near the open end thereof and fixed to said body. The portions of flexible material are detachably secured to a tape carrying flexible material. The tape is adhesively attached to the periphery of the cast.

5 Claims, 4 Drawing Figures

CAST SOCK

This invention relates to a toe covering or semi-sock for use in connection with a surgical cast when applied to a human foot and leg. More particularly, the invention relates to a toe covering comprising an open ended semi-sock portion of knitted textile fabric, adapted to receive the forward portion of the human foot extending beyond the cast and which when encasing the forward portion of the human foot extends over the forward portion of the cast and is detachably secured thereto.

Previous efforts to develop a cast sock have resulted in cumbersome unsightly designs which were difficult to apply, difficult to maintain in place when once applied and difficult to remove.

It is therefore an object of the present invention to provide a cast sock which is easy to apply, can be maintained readily in position when once applied and is easy to remove.

Another object is to provide a cast sock which is neat in appearance, presenting an over-all effect substantially similar to a conventional sock.

According to the invention the cast sock has uniformly spaced areas around the open end on the interior thereof which are capable of attaching themselves to a detachably receptive tape placed on the cast and around the foot.

This invention will now be described in more detail by reference to the attached drawing given by way of non-limiting example in which.

Figure 1:
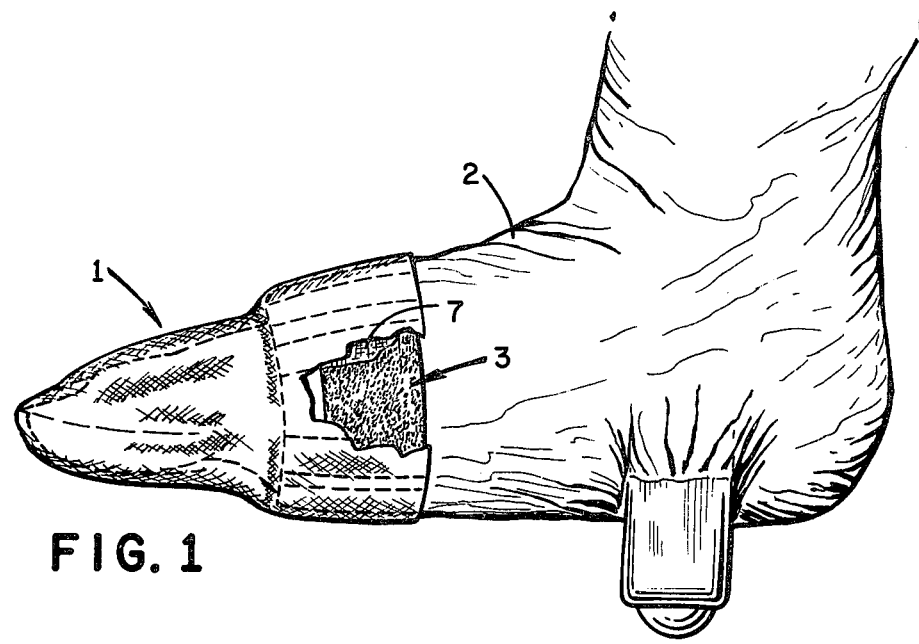
FIG. 1 is a side elevation view of the invention showing the cast sock applied to a human foot in a surgical walking cast.

Referring now to FIG. 1 of the drawing the cast sock 1 is shown applied to a surgical walking cast 2. The sock has been slipped over the exposed toes of the wearer and after adjustment for the convenience of the wearer is detachably secured to the peripheral front portion of the cast.

Figure 2:
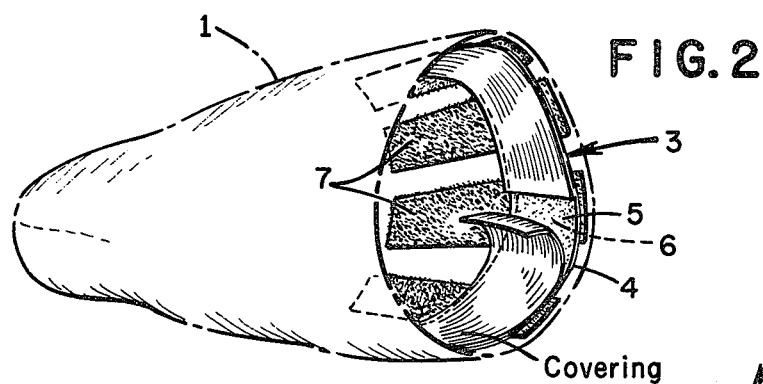
FIG. 2 is a perspective view of the cast sock with the tape attached thereto.

As shown in FIG. 2 a tape 3 is detachably secured to the interior of the sock near the open end thereof. Tape 3 is a laminate composed of a backing material 4 to one side of which there is applied a pressure sensitive adhesive 5 and to which other side there is applied a fastening means 6 which comprises a flexible gripping material (one of a set 6, 7) which may be either a male or female strip. The strip 6 extends the full length of the backing material which is of such a length as to completely circle the cast. The flexible gripping material may be attached to the backing material by any known means such as sewing, ironing-on or glueing. The laminate may be adhesive tape to which is fixed the flexible gripping material.

The tape is attached to the cast by means of the pressure sensitive adhesive. Although the tape may be placed at different uniform distances from the front edge of the cast depending upon the size of the sock to be applied it generally will be placed on the outer periphery of the cast at the front end thereof.

In order to prevent the tape from adhering to undesirable objects before being applied to the cast the tape may carry a removable or peel-off covering on the pressure sensitive adhesive.

Figure 3:
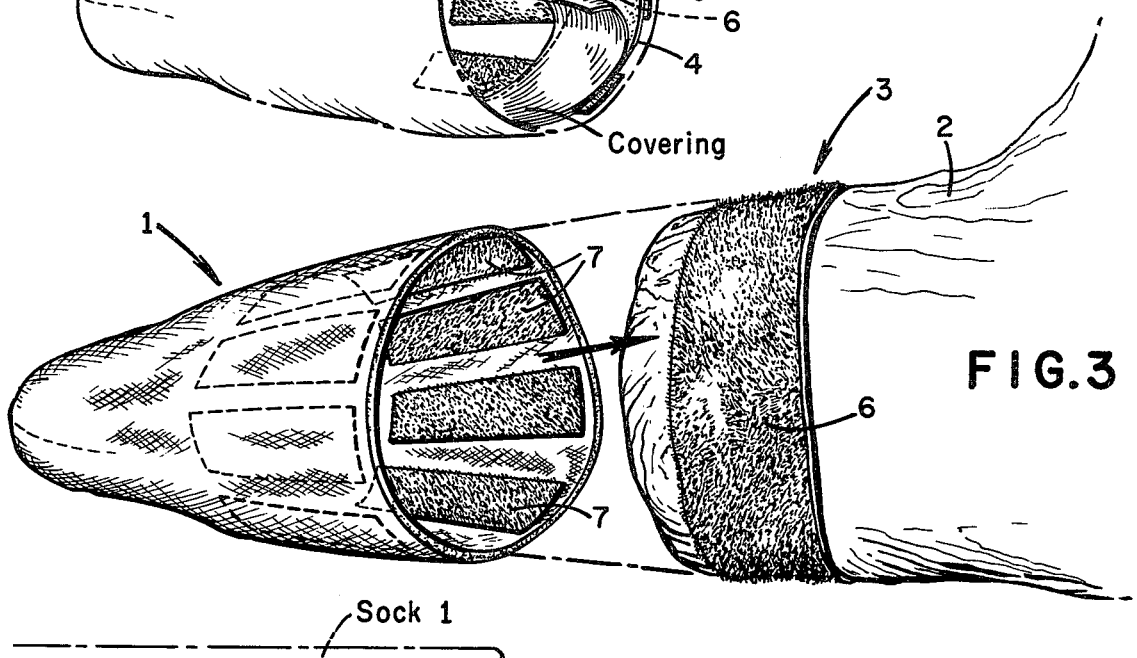
FIG. 3 is an exploded view of the cast sock of FIG. 1 with the tape on the cast.
Figure 4:
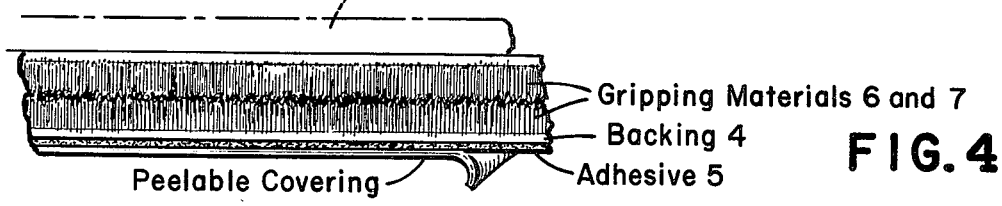
FIG. 4 is a sectional view of the tape.

As best seen in FIG. 3 there is disposed within the sock a series of portions 7 of flexible gripping material matable with the flexible gripping material of the tape. These portions may be uniformly or non-uniformly distributed around the interior of the sock at its open end. These portions also may be of any shape i.e. rectangular, square, oblong or triangular, provided that they are of sufficient length in the direction of the toe of the sock to permit some degree of adjustment in the tightness or looseness of the fit of the sock. Preferably they are of an elongated shape wherein the longer dimension extends from the edge of the open end of the sock toward the toe.

The sock may be made in several basic sizes, for children, ladies and men, but within these basic sizes the individual sock is to a degree adjustable to meet varying size requirements. The sock may be made from any material known for its use in hosiery such as polyamide, wool, polyester, cotton, silk, acrylic, rayon or combinations thereof.

In putting the sock on the foot the hands are utilized to expand or stretch the sock circumferentially to a size larger than the taped circumference of the cast, pull the sock over the tape and then release the sock so that all flexible gripping material portions contact the mating gripping material of the tape. The gripping material is of the type disclosed in U.S. Pat. No. 2,717,437. The operation of the gripping material for attaching or securing two members is well known so that it is unnecessary to describe further.

Although the invention has been herein shown and described in what is conceived to be the most practical and preferred embodiment, it is recognized that departures may be made therefrom within the scope of the invention, which is not to be limited to the details disclosed herein but is to be accorded the full scope of the claims so as to embrace any and all equivalent embodiments.

What is claimed is:

1. A reusable stretchable toe covering for use with a surgical cast comprising an open ended semi-sock body of knitted textile material, adapted to receive the forward portion of a human foot extending beyond the cast and portions of flexible gripping material spaced around the interior of the body near the open end thereof and fixed to said body, said gripping material being removably grippable to matable material independent of the stretchability of said knitted textile material.

2. A reusable stretchable toe covering for use with a surgical cast comprising an open ended semi-sock body of knitted textile material, adapted to receive the forward portion of a human foot extending beyond the cast, portions of flexible gripping material spaced around the interior of the body near the open end thereof and fixed to said body, and a laminate tape detachably secured to said portions of flexible gripping material, said tape comprising a backing material to one side of which is applied a pressure sensitive adhesive and to the other side of which is applied a flexible gripping material matable with said portions of material of said body.

3. The toe covering of claim 2, including a peel-off covering for the side of said tape carrying said pressure sensitive adhesive.

4. The toe covering of claim 1, wherein said portions of flexible gripping material are of an elongated shape, said material having its longer dimension extending from the edge of the open end toward the toe of said covering.

5. The toe covering of claim 2, wherein said portions of flexible gripping material are of an elongated shape, said material having its longer dimension extending from the edge of the open end toward the toe of said covering.

* * * * *